(12) United States Patent
Tong et al.

(10) Patent No.: US 10,279,056 B2
(45) Date of Patent: May 7, 2019

(54) LAMP DEVICE, SUBSTRATE CLEANING APPARATUS AND OPERATION METHOD THEREOF

(71) Applicants: BOE TECHNOLOGY GROUP CO., LTD., Beijing (CN); HEFEI XINSHENG OPTOELECTRONICS TECHNOLOGY CO., LTD., Hefei, Anhui (CN)

(72) Inventors: Qing Tong, Beijing (CN); Yong Yang, Beijing (CN); Weijing Liao, Beijing (CN)

(73) Assignees: BOE TECHNOLOGY GROUP CO., LTD., Beijing (CN); HEFEI XINSHENG OPTOELECTRONICS TECHNOLOGY CO., LTD., Hefei, Anhui (CN)

( * ) Notice: Subject to any disclaimer, the term of this patent is extended or adjusted under 35 U.S.C. 154(b) by 37 days.

(21) Appl. No.: 14/803,909

(22) Filed: Jul. 20, 2015

(65) Prior Publication Data
US 2016/0151522 A1    Jun. 2, 2016

(30) Foreign Application Priority Data

Nov. 28, 2014  (CN) .......................... 2014 1 0713454

(51) Int. Cl.
*A61L 2/10*  (2006.01)
(52) U.S. Cl.
CPC ............. *A61L 2/10* (2013.01); *A61L 2202/14* (2013.01)
(58) Field of Classification Search
CPC ........ A61L 2/00; A61L 2/0029; A61L 2/0047; A61L 2/0052; A61L 2/0058; A61L 2/08;
(Continued)

(56) References Cited

U.S. PATENT DOCUMENTS 3,619,590 A * 11/1971 Meulemans ....... G03B 15/0426
                                                          362/10
3,988,633 A * 10/1976 Shurgan ................ C03B 23/051
                                                          313/493
(Continued)

FOREIGN PATENT DOCUMENTS

CN        203656637 U      6/2014

OTHER PUBLICATIONS

The Second Office Action dated Jun. 22, 2017 corresponding to Chinese application No. 201410713454.3.

*Primary Examiner* — Jason L McCormack
(74) *Attorney, Agent, or Firm* — Nath, Goldberg & Meyer; Joshua B. Goldberg

(57) ABSTRACT

This invention provides a lamp device, a substrate cleaning apparatus and an operation method thereof, wherein the lamp device comprises a plurality of lamps and a plurality of connection structures, and every two adjacent lamps are provided with one connection structure therebetween, wherein each lamp is provided with a first recess and a second recess along a direction in which the plurality of lamps are arranged, one end of each connection structure is positioned into the first recess of one of two adjacent lamps and the other end of the connection structure is positioned into the second recess of the other one of the two adjacent lamps. With this configuration, the connection structures do not protrude from the surfaces of the far ultra-violet lamps, and thus the glass substrate is prevented from being scratched, and both the yield of the display panels and capacities of removing organic substances are increased.

18 Claims, 3 Drawing Sheets

(58) Field of Classification Search
CPC . A61L 2/084; A61L 2/085; A61L 2/10; A61L 9/18; A61L 9/20; A61L 12/063
USPC .............................. 250/491.1, 453.11, 455.11
See application file for complete search history.

(56) References Cited

U.S. PATENT DOCUMENTS

| | | | | | |
|---|---|---|---|---|---|
| 4,835,442 | A | * | 5/1989 | Sugimoto | H01J 5/48 313/17 |
| 5,168,999 | A | * | 12/1992 | Lee | B65D 25/105 206/420 |
| 6,059,110 | A | * | 5/2000 | Tseng | B65D 85/42 206/420 |
| 2004/0218386 | A1 | * | 11/2004 | Doll | H01J 5/54 362/219 |
| 2007/0231189 | A1 | * | 10/2007 | Jung | A61L 2/08 422/3 |
| 2010/0028201 | A1 | * | 2/2010 | Neister | A61L 2/0011 422/24 |
| 2010/0221155 | A1 | * | 9/2010 | Shimizu | A61L 2/10 422/186.05 |
| 2013/0004367 | A1 | * | 1/2013 | Roberts | A61L 2/10 422/24 |

* cited by examiner

LAMP DEVICE, SUBSTRATE CLEANING APPARATUS AND OPERATION METHOD THEREOF

FIELD OF THE INVENTION

The present invention relates to the field of display technology, and particularly to a lamp device, a substrate cleaning apparatus and an operation method thereof.

BACKGROUND OF THE INVENTION

In the process for cleaning substrates, a far ultra-violet apparatus is used to remove organic substances existing on the surface of the glass substrate. FIG. 1 is a structural diagram of a substrate cleaning apparatus in the prior art, FIG. 2 is an enlarged structural diagram of a portion A of the substrate cleaning apparatus in FIG. 1, and FIG. 3 is a structural diagram of a lamp device in FIG. 1. As shown in FIG. 1 to FIG. 3, the substrate cleaning apparatus comprises a first fixing end 101, a second fixing end 102 and a lamp device, one end of the lamp device is connected to the first fixing end 101, and the other end of the lamp device is connected to the second fixing end 102. The lamp device comprises a plurality of far ultra-violet lamps 103 and a plurality of connection structures 104, every two adjacent far ultra-violet lamps 103 are provided with one connection structure 104 therebetween for supporting the far ultra-violet lamps 103. The connection structures 104 are connected to other parts on the bottom surfaces of the far ultra-violet lamps 103 through fasteners (not shown in the figures), so that the far ultra-violet lamps 103 can be supported. A glass substrate 105 is provided below the far ultra-violet lamps 103, and the glass substrate 105 is provided on a plurality of bearing wheels 106.

The far ultra-violet apparatus is located at a latter portion of the cleaning process, and is positioned after an ultra-red unit and before a cooling unit. The ultra-red unit removes water vapor remained on the surface of the glass substrate 105 by means of high temperature, and the surface of the glass substrate 105 may have a temperature more than 100° C. after passing through the ultra-red unit. Since the connection structures 104 are exposed on the surfaces of the far ultra-violet lamps 103, distances between the connection structures 104 and the glass substrate 105 may be decreased due to the high temperature, thus the connection structures 104 are likely to be in contact with the surface of the glass substrate 105, so that the glass substrate 105 is likely to be scratched, which may affect the yield of the display panels.

SUMMARY OF THE INVENTION

To solve the problems that the glass substrate are scratched by the connection structures so that the yield of the display panels are affected, the present invention provides a lamp device, a substrate cleaning apparatus and an operation method thereof.

Therefore, the present invention provides a lamp device comprising a plurality of lamps and a plurality of connection structures, and every two adjacent lamps are provided with one connection structure therebetween, wherein each lamp is provided with a first recess and a second recess along a direction in which the plurality of lamps are arranged, one end of each connection structure is positioned into the first recess of one of two adjacent lamps and the other end of the connection structure is positioned into the second recess of the other one of the two adjacent lamps.

Preferably, the first recess and the second recess of each lamp are provided symmetrically.

Preferably, the first recess and the second recess of each lamp are provided at the bottom of the lamp.

Preferably, the first recess and the second recess of each lamp are provided at two opposite sides of the lamp.

Preferably, the lamps are far ultra-violet lamps.

The present invention further provides a substrate cleaning apparatus comprising a first fixing end, a second fixing end and the above lamp device, wherein one end of the lamp device is connected to the first fixing end, the other end of the lamp device is connected to the second fixing end, and the lamps radiate far ultra-violet rays to clean the substrate.

Preferably, the substrate cleaning apparatus further comprises a sensor, which is provided on the lamp and is used to detect a distance between the lamp and the substrate.

Optionally, there may be a plurality of sensors provided in the substrate cleaning apparatus.

Preferably, the substrate cleaning apparatus further comprises: an adjusting mechanism, which is connected to the sensor; and a controller, which is connected to the sensor and the adjusting mechanism, for controlling the adjusting mechanism to adjust the distance between the lamp and the substrate according to the distance between the lamp and the substrate detected by the sensor.

Preferably, the sensor includes a first sensor and a second sensor, and wherein the first sensor is provided on a portion of the lamp adjacent to the first fixing end, and the second sensor is provided on a portion of the lamp adjacent to the second fixing end.

Preferably, the adjusting mechanism includes a first adjusting mechanism connected to the first sensor and a second adjusting mechanism connected to the second sensor, wherein the controller is connected to the first sensor, the second sensor, the first adjusting mechanism and the second adjusting mechanism, and the controller receives a first distance between the lamp and the substrate detected by the first sensor and a second distance between the lamp and the substrate detected by the second sensor, respectively, and controls the first adjusting mechanism according to the first distance and controls the second adjusting mechanism according to the second distance to adjust the distance between the lamp and the substrate.

Preferably, the first adjusting mechanism includes a first adjusting slide block and a first motor, the second adjusting mechanism includes a second adjusting slide block and a second motor, the first adjusting slide block is connected to the first fixing end and the first motor, and the second adjusting slide block is connected to the second fixing end and the second motor, and wherein the controller compares the received first and second distances with a preset standard distance, and controls actions of the first motor and the second motor according to the comparison result;

the first motor is used to adjust the first distance through the first adjusting slide block under the control of the controller; and the second motor is used to adjust the second distance through the second adjusting slide block under the control of the controller.

Preferably, when the first distance is smaller than the standard distance, the controller controls the first motor to lift the first fixing end through the first adjusting slide block, and when the second distance is smaller than the standard distance, the controller controls the second motor to lift the second fixing end through the second adjusting slide block; or when the first distance is larger than the standard distance, the controller controls the first motor to decline the first fixing end through the first adjusting slide block, and when the second distance is larger than the standard distance, the controller controls the second motor to decline the second fixing end through the second adjusting slide block.

Preferably, the first adjusting slide block includes a first top wedge slide block and a first bottom wedge slide block which is below the first top wedge slide block, a wedge face of the first top wedge slide block is in slidable contact with a wedge face of the first bottom wedge slide block, the first top wedge slide block is connected to the bottom surface of the first fixing end, and the first bottom wedge slide block is connected to the first motor;

the second adjusting slide block includes a second top wedge slide block and a second bottom wedge slide block which is below the second top wedge slide block, a wedge face of the second top wedge slide block is in slidable contact with a wedge face of the second bottom wedge slide block, the second top wedge slide block is connected to the bottom surface of the second fixing end, and the second bottom wedge slide block is connected to the second motor;

so that the first bottom wedge slide block is driven by the first motor to move forward to drive the first top wedge slide block to move upwards;

the second bottom wedge slide block is driven by the second motor to move forward to drive the second top wedge slide block to move upwards;

the first bottom wedge slide block is driven by the first motor to move backwards to drive the first top wedge slide block to move downwards; or the second bottom wedge slide block is driven by the second motor to move backwards to drive the second top wedge slide block to move downwards.

The present invention further provides an operation method of a substrate cleaning apparatus, wherein the substrate cleaning apparatus comprises a first fixing end, a second fixing end and the lamp device of claim 5, wherein one end of the lamp device is connected to the first fixing end, the other end of the lamp device is connected to the second fixing end, and wherein the operation method comprises steps of:
providing a glass substrate below the lamp device; and
radiating far ultra-violet rays, by the lamp device, to the glass substrate.

Preferably, the substrate cleaning apparatus further comprises a sensor and a controller, the controller is connected to the sensor, the sensor is provided on the lamp, wherein the operation method further comprises a step of:

Detecting a distance between the lamp and the glass substrate, and transmitting the distance to the controller, by the sensor.

Preferably, the sensor further includes a first sensor and a second sensor, and wherein the first sensor is provided on a portion of the lamp adjacent to the first fixing end, and the second sensor is provided on a portion of the lamp adjacent to the second fixing end, and wherein the operation method further comprises steps of:

detecting a first distance between the lamp and the substrate, and transmitting the first distance to the controller, by the first sensor;

detecting a second distance between the lamp and the substrate, and transmitting the second distance to the controller, by the second sensor.

Preferably, the substrate cleaning apparatus further includes a first adjusting mechanism connected to the first sensor and a second adjusting mechanism connected to the second sensor, and the controller is connected to the first adjusting mechanism and the second adjusting mechanism, and wherein the operation method further comprises steps of:

comparing the first distance with a preset standard distance, and controlling the first adjusting mechanism according to the comparison result, by the controller; and comparing the second distance with a preset standard distance, and controlling the second adjusting mechanism according to the comparison result, by the controller.

Preferably, the first adjusting mechanism includes a first adjusting slide block and a first motor, the second adjusting mechanism includes a second adjusting slide block and a second motor, the first adjusting slide block is connected to the first fixing end and the first motor, and the second adjusting slide block is connected to the second fixing end and the second motor, and wherein the operation method further comprises steps of:

controlling action of the first motor according to the comparison result between the first distance and the preset standard distance, by the controller;

controlling action of the second motor according to the comparison result between the second distance and the preset standard distance, by the controller; and adjusting the first distance through the first adjusting slide block under the control of the controller, by the first motor; and adjusting the second distance through the second adjusting slide block under the control of the controller, by the second motor.

Preferably, the operation method further comprises steps of:

when the first distance is smaller than the standard distance, controlling the first motor to lift the first fixing end through the first adjusting slide block, by the controller, and when the second distance is smaller than the standard distance, controlling the second motor to lift the second fixing end through the second adjusting slide block, by the controller; or when the first distance is larger than the standard distance, controlling the first motor to decline the first fixing end through the first adjusting slide block, by the controller, and when the second distance is larger than the standard distance, controlling the second motor to decline the second fixing end through the second adjusting slide block, by the controller.

Preferably, the first adjusting slide block includes a first top wedge slide block and a first bottom wedge slide block which is below the first top wedge slide block, a wedge face of the first top wedge slide block is in slidable contact with a wedge face of the first bottom wedge slide block, the first top wedge slide block is connected to the bottom surface of the first fixing end, and the first bottom wedge slide block is connected to the first motor;

the second adjusting slide block includes a second top wedge slide block and a second bottom wedge slide block which is below the second top wedge slide block, a wedge face of the second top wedge slide block is in slidable contact with a wedge face of the second bottom wedge slide block, the second top wedge slide block is connected to the bottom surface of the second fixing end, and the second bottom wedge slide block is connected to the second motor;

wherein the steps of adjusting the first distance through the first adjusting slide block under the control of the controller, by the first motor and adjusting the second distance through the second adjusting slide block under the control of the controller, by the second motor further comprise steps of:

driving the first bottom wedge slide block, by the first motor, to move forward or backwards to drive the first top wedge slide block to move upwards or downwards; and driving the second bottom wedge slide block, by the second motor, to move forward or backwards to drive the second top wedge slide block to move upwards or downwards.

Advantages of the present invention are as follows:

In the lamp device, the substrate cleaning apparatus and the operation method thereof of the present invention, the lamp device comprises a plurality of lamps and a plurality of connection structures, every two adjacent lamps are provided with one connection structure therebetween, wherein each lamp is symmetrically provided with a first recess and a second recess along a direction in which the plurality of lamps are arranged, one end of each connection structure is positioned into the first recess of one of two adjacent lamps and the other end of the connection structure is positioned into the second recess of the other one of the two adjacent lamps, so that the connection structure does not protrude from the surface of the lamp, and thus the glass substrate is prevented from being scratched by the connection structure, and both the yield of the display panels and capacities of removing organic substances are increased.

DETAILED DESCRIPTION OF THE EMBODIMENTS

In order to make persons skilled in the art better understand solutions of the present invention, the lamp device, the substrate cleaning apparatus and the operation method thereof in the present invention will be described in detail below in conjunction with the drawings and embodiments.

First Embodiment

Figure 1:
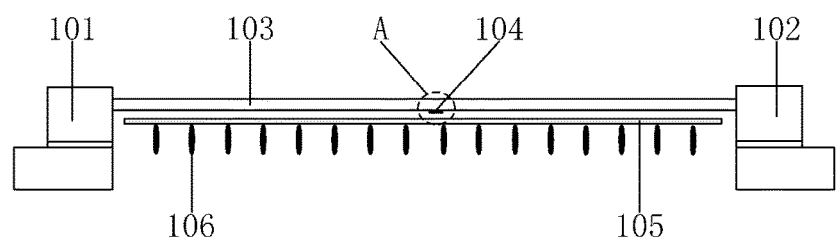
FIG. 1 is a structural diagram of a substrate cleaning apparatus in the prior art.
Figure 2:
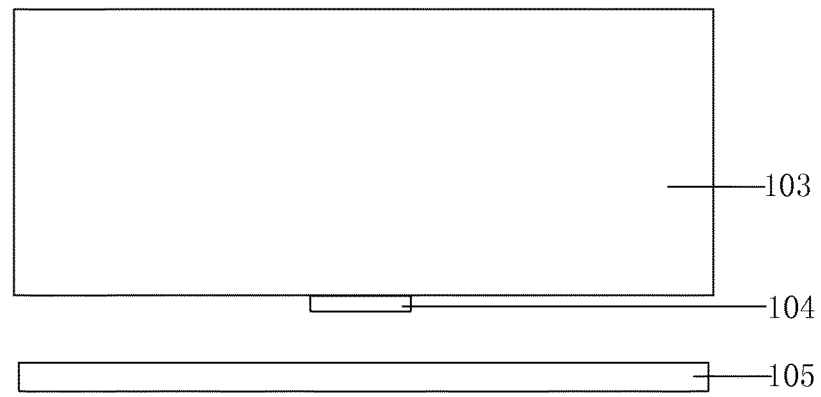
FIG. 2 is an enlarged structural diagram of a portion A of the substrate cleaning apparatus in FIG. 1.
Figure 3:
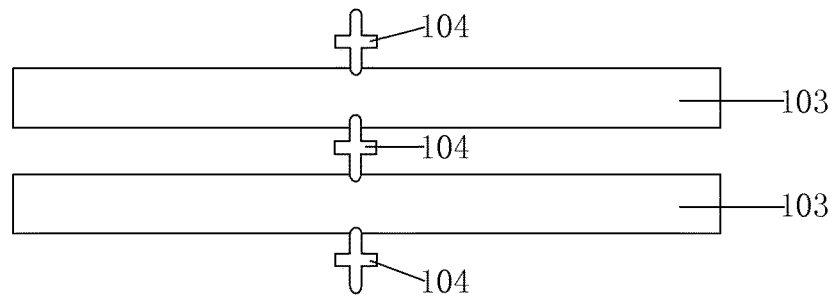
FIG. 3 is a structural diagram of a lamp device in FIG. 1.
Figure 4:
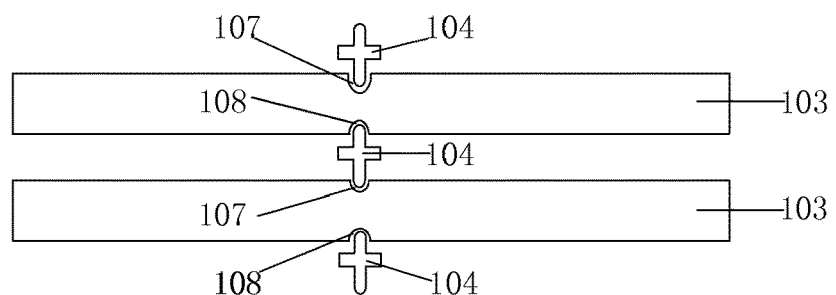
FIG. 4 is a structural diagram of a lamp device in a first embodiment of the present invention.

FIG. 4 is a structural diagram of a lamp device in a first embodiment of the present invention. As shown in FIG. 4, the lamp device comprises a plurality of far ultra-violet lamps 103 and a plurality of connection structures 104, and every two adjacent far ultra-violet lamps 103 are provided with one connection structure 104 therebetween. Each of the far ultra-violet lamps 103 is symmetrically provided with a first recess 107 and a second recess 108 along a direction in which the plurality of far ultra-violet lamps 103 are arranged. Preferably, the far ultra-violet lamp 103 and the recesses thereof are formed to be integrated. That is to say, the recesses 107 and 108 and the far ultra-violet lamp 103 are formed simultaneously. In the lamp device, one end of each connection structure 104 is positioned into the first recess 107 of one of two adjacent far ultra-violet lamps 103 and the other end of the connection structure 104 is positioned into the second recess 108 of the other one of the two adjacent far ultra-violet lamps 103. Each of the connection structures 104 is provided in the first recess 107 and the second recess 108 so as not to protrude from the surface of the far ultra-violet lamp 103 adjacent to the glass substrate, thus the glass substrate is prevented from being scratched by the connection structure 104, and both the yield of the display panels and capacities of removing organic substances are increased.

In this embodiment, the first recess 107 and the second recess 108 of each far ultra-violet lamp 103 are arranged opposite to each other, and both the first recess 107 and the second recess 108 are provided at the bottom of the far ultra-violet lamp 103. Optionally, the first recess 107 and the second recess 108 of each far ultra-violet lamp 103 are provided on two sides of the far ultra-violet lamp 103. By symmetrically providing the first recess 107 and the second recess 108 of each far ultra-violet lamp 103 at the bottom or two sides of the far ultra-violet lamp 103, the structure of the lamp device is simple, and cost thereof is low.

In the lamp device of the present embodiment, the lamp device comprises a plurality of far ultra-violet lamps and a plurality of connection structures, every two adjacent far ultra-violet lamps are provided with one connection structure therebetween, wherein each far ultra-violet lamp is symmetrically provided with a first recess and a second recess along a direction in which the plurality of far ultra-violet lamps are arranged, one end of each connection structure is positioned into the first recess of one of two adjacent far ultra-violet lamps and the other end of the connection structure is positioned into the second recess of the other one of the two adjacent far ultra-violet lamps, so that the connection structures do not protrude from the surfaces of the far ultra-violet lamps, and thus the glass substrate is prevented from being scratched by the connection structures, and both the yield of the display panels and capacities of removing organic substances are increased.

Second Embodiment

Figure 5:
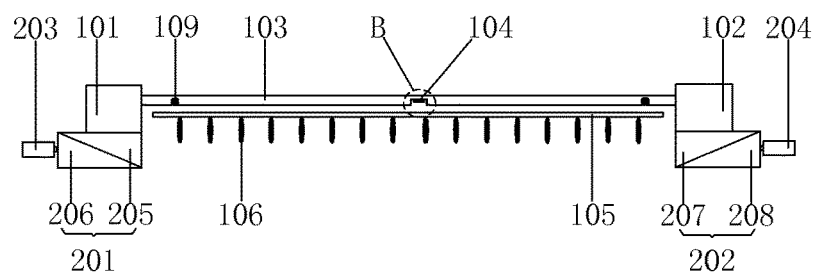
FIG. 5 is a structural diagram of a substrate cleaning apparatus in a second embodiment of the present invention.
Figure 6:
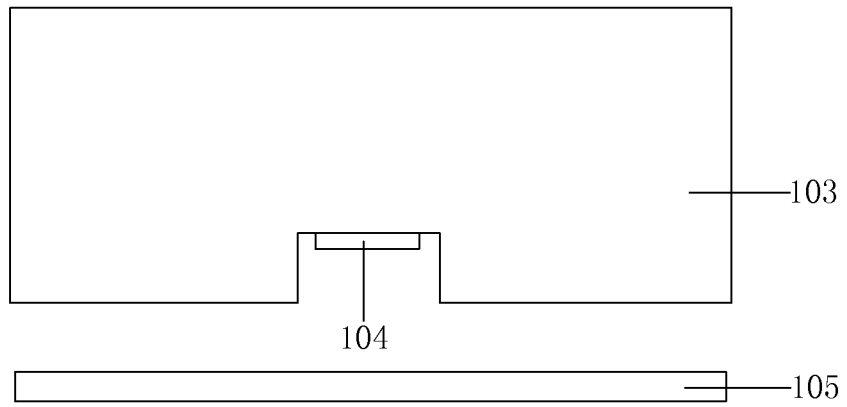
FIG. 6 is an enlarged structural diagram of a portion B of the substrate cleaning apparatus in FIG. 5.

FIG. 5 is a structural diagram of a substrate cleaning apparatus in a second embodiment of the present invention, and FIG. 6 is an enlarged structural diagram of a portion B of the substrate cleaning apparatus in FIG. 5. As shown in FIG. 5 and FIG. 6, the substrate cleaning apparatus comprises a first fixing end 101, a second fixing end 102 and the lamp device. One end of the lamp device is connected to the first fixing end 101, and the other end of the lamp device is connected to the second fixing end 102. With reference to FIG. 4, the lamp device comprises a plurality of far ultra-violet lamps 103 and a plurality of connection structures 104, and every two adjacent far ultra-violet lamps 103 are provided with one connection structure 104 therebetween. Each of the far ultra-violet lamps 103 is symmetrically provided with a first recess 107 and a second recess 108. One end of each connection structure 104 is positioned into the first recess 107 of one of two adjacent far ultra-violet lamps 103 and the other end of the connection structure 104 is positioned into the second recess 108 of the other one of the two adjacent far ultra-violet lamps 103. That is, each of the connection structures 104 is provided in the first recess 107 of one of two adjacent far ultra-violet lamps 103 and the second recess 108 of the other one of two adjacent far ultra-violet lamps 103. A plurality of bearing wheels 106 are provided below the far ultra-violet lamps 103 for supporting the glass substrate 105. The far ultra-violet lamps 103 radiate far ultra-violet rays to the glass substrate 105, so as to remove the organic substances on the glass substrate 105. Since the connection structure 104 is provided in the first recess 107 and the second recess 108 of the far ultra-violet lamp 103, so that the connection structure 104 does not protrude from the surface of the far ultra-violet lamp 103, and thus the glass substrate is prevented from being scratched by the connection structure 104, and both the yield of the display panels and capacities of removing organic substances are increased.

In this embodiment, the substrate cleaning apparatus further comprises a sensor 109, which is provided on the far ultra-violet lamp 103. Optionally, the sensor 109 is attached to one end of the far ultra-violet lamp 103 via a double-sided adhesive tape, so that influence on radiation from the far ultra-violet lamp 103 to the glass substrate therebelow can be avoided. Preferably, there are a plurality of sensors 109. Further preferably, there are two sensors 109 and these two sensors 109 are provided on the same far ultra-violet lamp 103, wherein one of these two sensors 109 is adjacent to the first fixing end 101, and the other one of these two sensors 109 is adjacent to the second fixing end 102. Certainly, these two sensors 109 may provided on different far ultra-violet lamps 103, so long as one of these two sensors 109 is adjacent to the first fixing end 101, and the other one of these two sensors 109 is adjacent to the second fixing end 102. The sensor 109 is used to measure a distance between far ultra-violet lamp 103 and the glass substrate 105. By means of the sensor 109, the substrate cleaning apparatus can automatically monitor the distance between the far ultra-violet lamp 103 and the glass substrate 105, so that operational security of the substrate cleaning apparatus can be ensured, and the capacities of removing the organic substances are increased. Preferably, each far ultra-violet lamp 103 may be provided with two sensors 109 like this. In addition, the sensor 109 may be provided on a surface of the far ultra-violet lamp 103 adjacent to the glass substrate 105, of course, the present invention is not limited thereto, the sensor 109 may be provided on other surface of the far ultra-violet lamp 103, so long as it can measure the distance between the far ultra-violet lamp 103 and the glass substrate 105.

In this embodiment, the substrate cleaning apparatus further comprises: an adjusting mechanism, which is connected to the sensor; and a controller (not shown in Figures), which is connected to the sensor 109 and the adjusting mechanism, for controlling the adjusting mechanism to adjust the distance between the far ultra-violet lamp 103 and the glass substrate 105 according to the distance between the far ultra-violet lamp 103 and the glass substrate 105 measured by the sensor 109.

Specifically, the adjusting mechanism includes a first adjusting mechanism and a second adjusting mechanism. More specifically, the first adjusting mechanism includes a first adjusting slide block 201 and a first motor 203; and the second adjusting mechanism includes a second adjusting slide block 202 and a second motor 204. The first adjusting slide block 201 is connected to the first fixing end 101 and the first motor 203, and the second adjusting slide block 202 is connected to the second fixing end 102 and the second motor 204. The sensor 109 is also used to transmit the measured distance to the controller. The controller is used to compare the received distance with a preset standard distance, and controls actions of the first motor 203 and the second motor 204 according to the comparison result. That is, the first motor 203 is used to adjust the distance between the far ultra-violet lamp 103 and the glass substrate 105 through the first adjusting slide block 201 under the control of the controller; and the second motor 204 is used to adjust the distance between the far ultra-violet lamp 103 and the glass substrate 105 through the second adjusting slide block 202 under the control of the controller.

In the practical application, when the measured distance is smaller than the preset standard distance, the controller controls the first motor 203 to lift the first fixing end 101 through the first adjusting slide block 201, at the same time, the controller controls the second motor 204 to lift the second fixing end 102 through the second adjusting slide block 202. When the measured distance is larger than the preset standard distance, the controller controls the first motor 203 to decline the first fixing end 101 through the first adjusting slide block 201, and at the same time, the controller controls the second motor 204 to decline the second fixing end 102 through the second adjusting slide block 202.

More specifically, the sensor 109 adjacent to the first fixing end 101 (a first sensor 109) transmits the measured distance (a first distance) to the controller. The controller compares the received first distance with the preset standard distance, and controls the first motor 203 according to the comparison result. If the first distance is smaller than the standard distance, the controller controls the first motor 203 to lift the first fixing end 101 through the first adjusting slide block 201. Otherwise, if the first distance is larger than the standard distance, the controller controls the first motor 203 to decline the first fixing end 101 through the first adjusting slide block 201.

As such, the sensor adjacent to the second fixing end 102 (a second sensor 109) transmits the measured distance (a second distance) to the controller. The controller compares the received second distance with the preset standard distance, and controls the second motor 204 according to the comparison result. If the second distance is smaller than the standard distance, the controller controls the second motor 204 to lift the second fixing end 102 through the second adjusting slide block 202. Otherwise, if the second distance is larger than the standard distance, the controller controls the second motor 204 to decline the second fixing end 102 through the second adjusting slide block 202.

It can be seen from above that, when the sensors 109 provided near two ends of the far ultra-violet lamp 103 respectively detect different distances, the controller may separately control lift or decline of the first fixing end 101 and the second fixing end 102 according to the comparison results between the measured distances and the standard distance. Therefore, the distance between the far ultra-violet lamp 103 and the glass substrate 105 may be proper.

In this embodiment, the first adjusting slide block 201 includes a first top wedge slide block 205 and a first bottom wedge slide block 206 which is below the first top wedge slide block 205, a wedge face of the first top wedge slide block 205 is in slidable contact with a wedge face of the first bottom wedge slide block 206, the first top wedge slide block 205 is connected to the bottom surface of the first fixing end 101, and an outer side of the first bottom wedge slide block 206 is connected to the first motor 203. The second adjusting slide block 202 includes a second top wedge slide block 207 and a second bottom wedge slide block 208 which is below the second top wedge slide block 207, a wedge face of the second top wedge slide block 207 is in slidable contact with a wedge face of the second bottom wedge slide block 208, the second top wedge slide block 207 is connected to the bottom surface of the second fixing end 102, and an outer side of the second bottom wedge slide block 208 is connected to the second motor 204.

Specifically, the first bottom wedge slide block 206 is driven by the first motor 203 to move forward to drive the first top wedge slide block 205 to move upwards, so that height of the first fixing end 101 is increased. The first bottom wedge slide block 206 is driven by the first motor 203 to move backwards to drive the first top wedge slide block 205 to move downwards, so that the height of the first fixing end 101 is reduced. The second bottom wedge slide block 208 is driven by the second motor 204 to move forward to drive the second top wedge slide block 207 to move upwards, so that height of the second fixing end 102 is increased. The second bottom wedge slide block 208 is driven by the second motor 204 to move backwards to drive the second top wedge slide block 207 to move downwards, so that the height of the second fixing end 102 is reduced. The substrate cleaning apparatus can automatically adjust and monitor the distance between the far ultra-violet lamp 103 and the glass substrate 105 through adjusting the heights of the first fixing end 101 and the second fixing end 102.

In the substrate cleaning apparatus of the present invention, the lamp device comprises a plurality of far ultra-violet lamps and a plurality of connection structures, every two adjacent far ultra-violet lamps are provided with one connection structure therebetween, wherein each far ultra-violet lamp is symmetrically provided with a first recess and a second recess along a direction in which the plurality of far ultra-violet lamps are arranged, one end of each connection structure is positioned into the first recess of one of two adjacent far ultra-violet lamps and the other end of the connection structure is positioned into the second recess of the other one of the two adjacent far ultra-violet lamps, so that the connection structure does not protrude from the surface of the far ultra-violet lamp, and thus the glass substrate is prevented from being scratched by the connection structure, and both the yield of the display panels and capacities of removing organic substances are increased.

Third Embodiment

Figure 7:
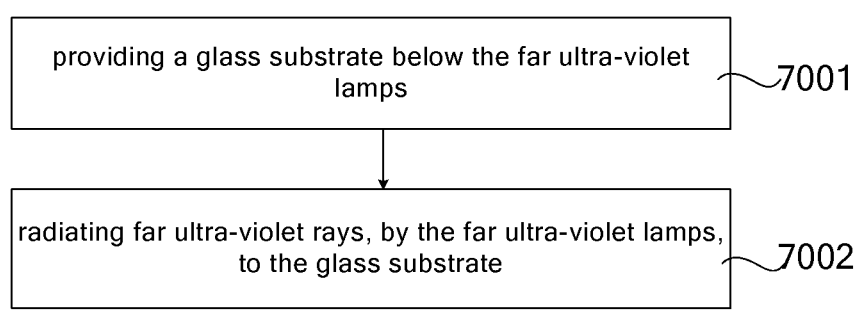
FIG. 7 is a flowchart diagram of an operation method of a substrate cleaning apparatus in a third embodiment of the present invention.

FIG. 7 is a flowchart diagram of an operation method of a substrate cleaning apparatus in a third embodiment of the present invention. As shown in FIG. 7, the operation method comprises:

Step 7001, providing a glass substrate below the far ultra-violet lamps.

In this embodiment, as shown in FIG. 5 and FIG. 6, the substrate cleaning apparatus comprises a first fixing end 101, a second fixing end 102 and the lamp device. One end of the lamp device is connected to the first fixing end 101, and the other end of the lamp device is connected to the second fixing end 102. With reference to FIG. 4, the lamp device comprises a plurality of far ultra-violet lamps 103 and a plurality of connection structures 104, every two adjacent far ultra-violet lamps 103 are provided with one connection structure 104 therebetween. Each of the far ultra-violet lamps 103 is symmetrically provided with a first recess 107 and a second recess 108. One end of the connection structure 104 is positioned into the first recess 107 of one of two adjacent far ultra-violet lamps 103 and the other end of the connection structure 104 is positioned into the second recess 108 of the other one of two adjacent far ultra-violet lamps 103. Optionally, a plurality of bearing wheels 106 are provided below the far ultra-violet lamps 103 for supporting the glass substrate 105.

Step 7002, radiating far ultra-violet rays, by the far ultra-violet lamps, to the glass substrate.

In this embodiment, the far ultra-violet lamps 103 radiate far ultra-violet rays to the glass substrate 105, so as to remove the organic substances on the glass substrate 105. At the same time, since the connection structure 104 is provided in the first recess 107 and the second recess 108, so that the connection structure 104 does not protrude from the surface of the far ultra-violet lamp 103, and thus the glass substrate is prevented from being scratched by the connection structure, and both the yield of the display panels and capacities of removing organic substances are increased.

In the practical application, the substrate cleaning apparatus further comprises a sensor 109, a first adjusting slide block 201, a first motor 203, a second adjusting slide block 202, a second motor 204 and a controller. The first adjusting slide block 201 is connected to the first fixing end 101 and the first motor 203, and the second adjusting slide block 202 is connected to the second fixing end 102 and the second motor 204.

With reference to FIG. 5 and FIG. 6, the sensor 109 measures the distance between the far ultra-violet lamp 103 and the glass substrate 105, and transmits the measured distance to the controller. The controller compares the received distance with a preset standard distance, and controls actions of the first motor 203 and the second motor 204 according to the comparison result. That is, the first motor 203 is used to adjust the distance between the far ultra-violet lamp 103 and the glass substrate 105 through the first adjusting slide block 201 under the control of the controller; and the second motor 204 is used to adjust the distance between the far ultra-violet lamp 103 and the glass substrate 105 through the second adjusting slide block 202 under the control of the controller.

In a practical application, when the measured distance is smaller than the preset standard distance, the controller controls the first motor 203 to lift the first fixing end 101 through the first adjusting slide block 201, and at the same time, the controller controls the second motor 204 to lift the second fixing end 102 through the second adjusting slide block 202. When the measured distance is larger than the preset standard distance, the controller controls the first motor 203 to decline the first fixing end 101 through the first adjusting slide block 201, and at the same time, the controller controls the second motor 204 to decline the second fixing end 102 through the second adjusting slide block 202.

In another practical application, two sensors 109 are provided on the same far ultra-violet lamp 103, wherein one of the sensors 109 is adjacent to the first fixing end 101, and the other one of the sensors 109 is adjacent to the second fixing end 102.

More specifically, the sensor adjacent to the first fixing end 101 (a first sensor 109) transmits the measured distance (a first distance) to the controller. The controller compares the received first distance with the preset standard distance, and controls the first motor 203 according to the comparison result. If the first distance is smaller than the standard distance, the controller controls the first motor 203 to lift the first fixing end 101 through the first adjusting slide block 201. Otherwise, if the first distance is larger than the standard distance, the controller controls the first motor 203 to decline the first fixing end 101 through the first adjusting slide block 201.

As such, the sensor adjacent to the second fixing end 102 (a second sensor 109) transmits the measured distance (a second distance) to the controller. The controller compares the received second distance with the preset standard distance, and controls the second motor 204 according to the comparison result. If the second distance is smaller than the standard distance, the controller controls the second motor 204 to lift the second fixing end 102 through the second adjusting slide block 202. Otherwise, if the second distance is larger than the standard distance, the controller controls the second motor 204 to decline the second fixing end 102 through the second adjusting slide block 202.

It can be seen from above that, when the sensors 109 provided near two ends of the far ultra-violet lamp 103 respectively detect different distances, the controller may separately control lift or decline of the first fixing end 101 and the second fixing end 102 according to the comparison results between the measured distances and the standard distance. Therefore, the distance between the far ultra-violet lamp 103 and the glass substrate 105 may be proper.

In this embodiment, the first adjusting slide block 201 includes a first top wedge slide block 205 and a first bottom wedge slide block 206 which is below the first top wedge slide block 205, a wedge face of the first top wedge slide block 205 is in slidable contact with a wedge face of the first bottom wedge slide block 206, the first top wedge slide block 205 is connected to the bottom surface of the first fixing end 101, and an outer side of the first bottom wedge slide block 206 is connected to the first motor 203. The second adjusting slide block 202 includes a second top wedge slide block 207 and a second bottom wedge slide block 208 which is below the second top wedge slide block 207, a wedge face of the second top wedge slide block 207 is in slidable contact with a wedge face of the second bottom wedge slide block 208, the second top wedge slide block 207 is connected to the bottom surface of the second fixing end 102, and an outer side of the second bottom wedge slide block 208 is connected to the second motor 204.

Specifically, the first bottom wedge slide block 206 is driven by the first motor 203 to move forward to drive the first top wedge slide block 205 to move upwards, so that height of the first fixing end 101 is increased. The first bottom wedge slide block 206 is driven by the first motor 203 to move backwards to drive the first top wedge slide block 205 to move downwards, so that the height of the first fixing end 101 is reduced. The second bottom wedge slide block 208 is driven by the second motor 204 to move forward to drive the second top wedge slide block 207 to move upwards, so that height of the second fixing end 102 is increased. The second bottom wedge slide block 208 is driven by the second motor 204 to move backwards to drive the second top wedge slide block 207 to move downwards, so that the height of the second fixing end 102 is reduced. The substrate cleaning apparatus can automatically adjust and monitor the distance between the far ultra-violet lamps 103 and the glass substrate 105 through adjusting the heights of the first fixing end 101 and the second fixing end 102.

In the operation method of the substrate cleaning apparatus of the invention, the lamp device comprises a plurality of far ultra-violet lamps and a plurality of connection structures, every two adjacent far ultra-violet lamps are provided with one connection structure therebetween, wherein each far ultra-violet lamp is symmetrically provided with a first recess and a second recess along a direction in which the plurality of lamps are arranged, one end of each connection structure is positioned into the first recess of one of two adjacent far ultra-violet lamps and the other end of the connection structure is positioned into the second recess of the other one of the two adjacent far ultra-violet lamps, so that the connection structure does not protrude from the surface of the far ultra-violet lamp, and thus the glass substrate is prevented from being scratched by the connection structure, and both the yield of the display panels and capacities of removing organic substances are increased.

It should be understood that, the above embodiments are only exemplary embodiments used to explain the principle of the present invention and the protection scope of the present invention is not limited thereto. The person skilled in the art can make various variations and modifications without departing from the spirit and scope of the present invention, and these variations and modifications should be considered to belong to the protection scope of the invention.

The invention claimed is:

1. A lamp device comprising a plurality of lamps and a plurality of connection structures, wherein every two adjacent lamps are provided with one connection structure therebetween, and wherein each lamp is provided with a first recess and a second recess along a direction in which the plurality of lamps are arranged, the first recess and the second recess are recessed from a light emitting surface of the lamp, and one end of each connection structure is positioned into the first recess of one of two adjacent lamps to support the one of the two adjacent lamps, and the other end of the connection structure is positioned into the second recess of the other one of the two adjacent lamps to support the other one of the two adjacent lamps, wherein each connection structure is provided at a light-emitting side of one of the two adjacent lamps, wherein the first recess and the second recess of each lamp are provided symmetrically; and wherein the first recess and the second recess of each lamp are provided at the bottom of the lamp.

2. The lamp device of claim 1, wherein the first recess and the second recess of each lamp are provided at two opposite sides of the lamp.

3. The lamp device of claim 1, wherein the lamps are far ultra-violet lamps.

4. A substrate cleaning apparatus comprising a first fixing end, a second fixing end and the lamp device of claim 3, wherein one end of the lamp device is connected to the first fixing end, the other end of the lamp device is connected to the second fixing end, and the lamps radiate far ultra-violet rays to clean the substrate.

5. The substrate cleaning apparatus of claim 4, further comprising a sensor, which is provided on the lamp and is used to detect a distance between the lamp and the substrate.

6. The substrate cleaning apparatus of claim 5, further comprising:

an adjusting mechanism, which is connected to the sensor; and a controller, which is connected to the sensor and the adjusting mechanism, for controlling the adjusting mechanism to adjust the distance between the lamp and the substrate according to the distance between the lamp and the substrate detected by the sensor.

7. The substrate cleaning apparatus of claim 6, wherein the sensor includes a first sensor and a second sensor, and wherein the first sensor is provided on a portion of the lamp adjacent to the first fixing end, and the second sensor is provided on a portion of the lamp adjacent to the second fixing end.

8. The substrate cleaning apparatus of claim 7, wherein the adjusting mechanism includes a first adjusting mechanism connected to the first sensor and a second adjusting mechanism connected to the second sensor, wherein the controller is connected to the first sensor, the second sensor, the first adjusting mechanism and the second adjusting mechanism, and the controller receives a first distance between the lamp and the substrate detected by the first sensor and a second distance between the lamp and the substrate detected by the second sensor, respectively, and controls the first adjusting mechanism according to the first distance and controls the second adjusting mechanism according to the second distance to adjust the distance between the lamp and the substrate.

9. The substrate cleaning apparatus of claim 8, wherein the first adjusting mechanism includes a first adjusting slide block and a first motor, the second adjusting mechanism includes a second adjusting slide block and a second motor, the first adjusting slide block is connected to the first fixing end and the first motor, and the second adjusting slide block is connected to the second fixing end and the second motor, and wherein the controller compares the received first and second distances with a preset standard distance, and controls actions of the first motor and the second motor according to the comparison result;

the first motor is used to adjust the first distance through the first adjusting slide block under the control of the controller; and the second motor is used to adjust the second distance through the second adjusting slide block under the control of the controller.

10. The substrate cleaning apparatus of claim 9, wherein when the first distance is smaller than the standard distance, the controller controls the first motor to lift the first fixing end through the first adjusting slide block, and when the second distance is smaller than the standard distance, the controller controls the second motor to lift the second fixing end through the second adjusting slide block; or when the first distance is larger than the standard distance, the controller controls the first motor to decline the first fixing end through the first adjusting slide block, and when the second distance is larger than the standard distance, the controller controls the second motor to decline the second fixing end through the second adjusting slide block.

11. The substrate cleaning apparatus of claim 9, wherein the first adjusting slide block includes a first top wedge slide block and a first bottom wedge slide block which is below the first top wedge slide block, a wedge face of the first top wedge slide block is in slidable contact with a wedge face of the first bottom wedge slide block, the first top wedge slide block is connected to the bottom surface of the first fixing end, and the first bottom wedge slide block is connected to the first motor; and the second adjusting slide block includes a second top wedge slide block and a second bottom wedge slide block which is below the second top wedge slide block, a wedge face of the second top wedge slide block is in slidable contact with a wedge face of the second bottom wedge slide block, the second top wedge slide block is connected to the bottom surface of the second fixing end, and the second bottom wedge slide block is connected to the second motor;

so that the first bottom wedge slide block is driven by the first motor to move forward to drive the first top wedge slide block to move upwards;

the second bottom wedge slide block is driven by the second motor to move forward to drive the second top wedge slide block to move upwards;

the first bottom wedge slide block is driven by the first motor to move backwards to drive the first top wedge slide block to move downwards; or the second bottom wedge slide block is driven by the second motor to move backwards to drive the second top wedge slide block to move downwards.

12. An operation method of a substrate cleaning apparatus, wherein the substrate cleaning apparatus comprises a first fixing end, a second fixing end and the lamp device of claim 3, wherein one end of the lamp device is connected to the first fixing end, and the other end of the lamp device is connected to the second fixing end, and wherein the operation method comprises steps of:

providing a glass substrate below the lamp device; and radiating far ultra-violet rays, by the lamp device, to the glass substrate.

13. The operation method of claim 12, wherein the substrate cleaning apparatus further comprises a sensor and a controller, the controller is connected to the sensor, the sensor is provided on the lamp, wherein the operation method further comprises a step of:

detecting a distance between the lamp and the glass substrate, and transmitting the distance to the controller, by the sensor.

14. The operation method of claim 13, wherein the sensor further includes a first sensor and a second sensor, and wherein the first sensor is provided on a portion of the lamp adjacent to the first fixing end, and the second sensor is provided on a portion of the lamp adjacent to the second fixing end, and wherein the operation method further comprises steps of:

detecting a first distance between the lamp and the substrate, and transmitting the first distance to the controller, by the first sensor;

detecting a second distance between the lamp and the substrate, and transmitting the second distance to the controller, by the second sensor.

15. The operation method of claim 14, wherein the substrate cleaning apparatus further includes a first adjusting mechanism connected to the first sensor and a second adjusting mechanism connected to the second sensor, and the controller is connected to the first adjusting mechanism and the second adjusting mechanism, and wherein the operation method further comprises steps of:

comparing the first distance with a preset standard distance, and controlling the first adjusting mechanism according to the comparison result, by the controller; and comparing the second distance with a preset standard distance, and controlling the second adjusting mechanism according to the comparison result, by the controller.

16. The operation method of claim 15, wherein the first adjusting mechanism includes a first adjusting slide block and a first motor, the second adjusting mechanism includes a second adjusting slide block and a second motor, the first adjusting slide block is connected to the first fixing end and the first motor, and the second adjusting slide block is connected to the second fixing end and the second motor, and wherein the operation method further comprises steps of:

controlling action of the first motor according to the comparison result between the first distance and the preset standard distance, by the controller;

controlling action of the second motor according to the comparison result between the second distance and the preset standard distance, by the controller; and adjusting the first distance through the first adjusting slide block under the control of the controller, by the first motor; and adjusting the second distance through the second adjusting slide block under the control of the controller, by the second motor.

17. The operation method of claim 16, further comprising steps of:

when the first distance is smaller than the standard distance, controlling the first motor to lift the first fixing end through the first adjusting slide block, by the controller, and when the second distance is smaller than the standard distance, controlling the second motor to lift the second fixing end through the second adjusting slide block, by the controller; or when the first distance is larger than the standard distance, controlling the first motor to decline the first fixing end through the first adjusting slide block, by the controller, and when the second distance is larger than the standard distance, controlling the second motor to decline the second fixing end through the second adjusting slide block, by the controller.

18. The operation method of claim 16, wherein the first adjusting slide block includes a first top wedge slide block and a first bottom wedge slide block which is below the first top wedge slide block, a wedge face of the first top wedge slide block is in slidable contact with a wedge face of the first bottom wedge slide block, the first top wedge slide block is connected to the bottom surface of the first fixing end, and the first bottom wedge slide block is connected to the first motor;

the second adjusting slide block includes a second top wedge slide block and a second bottom wedge slide block which is below the second top wedge slide block, a wedge face of the second top wedge slide block is in slidable contact with a wedge face of the second bottom wedge slide block, the second top wedge slide block is connected to the bottom surface of the second fixing end, and the second bottom wedge slide block is connected to the second motor;

wherein the steps of adjusting the first distance through the first adjusting slide block under the control of the controller, by the first motor and adjusting the second distance through the second adjusting slide block under the control of the controller, by the second motor further comprise steps of:

driving the first bottom wedge slide block, by the first motor, to move forward or backwards to drive the first top wedge slide block to move upwards or downwards; and driving the second bottom wedge slide block, by the second motor, to move forward or backwards to drive the second top wedge slide block to move upwards or downwards.

* * * * *